US008646451B2

(12) United States Patent
Mistler

(10) Patent No.: US 8,646,451 B2
(45) Date of Patent: *Feb. 11, 2014

(54) CONDOM

(76) Inventor: William Thomas Mistler, Media, PA (US)

(*) Notice: Subject to any disclaimer, the term of this patent is extended or adjusted under 35 U.S.C. 154(b) by 666 days.

This patent is subject to a terminal disclaimer.

(21) Appl. No.: 12/642,897

(22) Filed: Dec. 21, 2009

(65) Prior Publication Data

US 2011/0041856 A1    Feb. 24, 2011

Related U.S. Application Data

(63) Continuation-in-part of application No. 11/983,022, filed on Nov. 6, 2007, now Pat. No. 7,673,632.

(51) Int. Cl.
*A61F 6/02* (2006.01)
*A61F 5/44* (2006.01)
*B65D 85/08* (2006.01)
*B65D 85/14* (2006.01)

(52) U.S. Cl.
USPC ........... 128/844; 128/842; 128/917; 128/918; 206/69; 604/346; 604/347; 604/349; 427/2.3

(58) Field of Classification Search
USPC .......... 128/842, 844, 917, 918; 604/346, 347, 604/349; 206/69; 427/2.3
See application file for complete search history.

(56) References Cited

U.S. PATENT DOCUMENTS

| | | | |
|---|---|---|---|
| 2,567,926 A | 9/1951 | Dunkelberger | |
| 2,670,736 A * | 3/1954 | Dunkelberger | 128/844 |
| 4,840,188 A | 6/1989 | Heidenfelder | |
| 4,920,983 A | 5/1990 | Jimenez et al. | |
| 5,018,532 A * | 5/1991 | Etheredge, III | 128/844 |
| 5,044,492 A | 9/1991 | Auerbach | |
| 5,163,448 A | 11/1992 | Foldesy | |
| 5,411,034 A | 5/1995 | Beck et al. | |

(Continued)

FOREIGN PATENT DOCUMENTS

| | | |
|---|---|---|
| CN | 1099996 | 3/1995 |
| FR | 2750318 | 1/1998 |
| JP | 7100160 | 4/1995 |
| JP | 8089524 | 4/1996 |

OTHER PUBLICATIONS http://flipeasy.mazdaq.com/splash.asp, Flipeasy.com, Jul. 9, 2008, website screen shot.

*Primary Examiner* — Patricia Bianco
*Assistant Examiner* — Brandon L Jackson
(74) *Attorney, Agent, or Firm* — Eckert Seamans Cherin & Mellott, LLC; David C. Jenkins

(57) ABSTRACT

A condom having an indicia disposed on the lower side of the roll when the condom is in the rolled configuration. Preferably, the indicia is a fluorescent marking disposed on the inner side of the condom disposed at a location so that, when the condom is in the rolled configuration, the indicia is visible from the lower side only. More preferably, the indicia is a ring-shaped marking extending about the inner side of the tubular body. In this configuration, a user holding a rolled condom can easily determine which is the upper side of the roll and which is the lower side of the roll. The user may then quickly orient the condom with the lower side facing toward the penis and unroll the condom in the proper direction.

8 Claims, 11 Drawing Sheets

(56) References Cited

U.S. PATENT DOCUMENTS

| | | |
|---|---|---|
| 5,454,379 A | 10/1995 | Shepherd |
| 5,666,972 A | 9/1997 | Gifford |
| 5,715,839 A | 2/1998 | Strauss et al. |
| 5,758,659 A * | 6/1998 | Thompson .................... 128/844 |
| 5,829,440 A | 11/1998 | Broad, Jr. |
| 5,965,276 A | 10/1999 | Shlenker et al. |
| 6,135,112 A * | 10/2000 | Harrison et al. ............. 128/844 |
| 6,308,708 B2 | 10/2001 | Strauss et al. |
| 6,321,751 B1 * | 11/2001 | Strauss et al. ................ 128/844 |
| 6,367,477 B2 * | 4/2002 | Lee ............................... 128/842 |
| D484,235 S | 12/2003 | Strenk et al. |
| 6,732,736 B2 | 5/2004 | Sanchez |
| 6,895,968 B2 | 5/2005 | Shapiro et al. |
| 6,929,118 B1 | 8/2005 | Izz |
| 7,121,281 B2 | 10/2006 | Tsugawa |
| 2006/0048784 A1 * | 3/2006 | Turner .......................... 128/844 |
| 2006/0134611 A1 | 6/2006 | Danzy |
| 2007/0181134 A1 | 8/2007 | Lang |
| 2008/0142021 A1 * | 6/2008 | Hook ............................ 128/844 |
| 2009/0090368 A1 | 4/2009 | Attila |
| 2009/0205668 A1 | 8/2009 | Morissette |

* cited by examiner

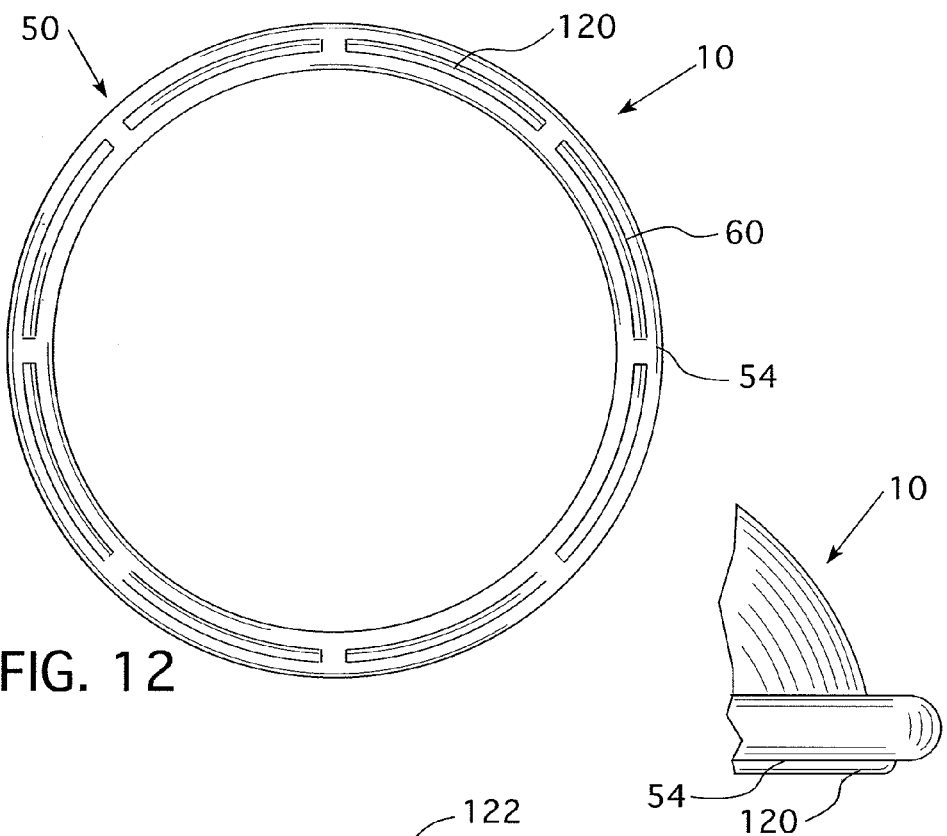
FIG. 12
FIG. 12A
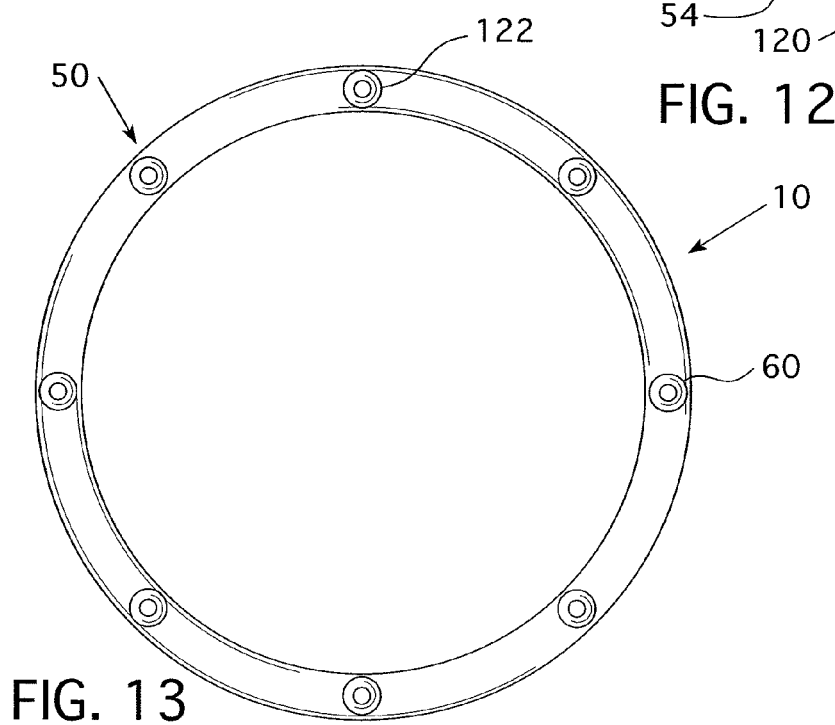
FIG. 13

CONDOM

CROSS REFERENCE TO RELATED APPLICATION

This is a continuation-in-part application claiming priority under 35 U.S.C. §119(e) to U.S. patent application Ser. No. 11/983,022, filed Nov. 6, 2007, now U.S. Pat. No. 7,673,632, entitled CONDOM.

BACKGROUND OF THE INVENTION

1. Field of the Invention

This invention relates to a condom and, more specifically, to a condom having an indicia indicating the proper orientation for use.

2. Background Information

Condoms are well known prophylactic devices. The condom is typically made from latex or another plastic, however, natural condoms are still in use. A condom includes a thin, elastic, generally tubular body having an open first end, an elongated medial section, and a closed second end section thereby defining a partially enclosed space. Further, the body, as well as each of the elements set forth in the prior sentence, has an inner side and an outer side. Typically, the open end includes an elastic ring or rib. When used, the penis is disposed in the partially enclosed space with the inner side of the condom contacting the penis.

While condoms are used in an unrolled, or unfurled, configuration, condoms are typically stored in a rolled configuration. The rolled configuration is created by rolling the rib over the outer side of the body medial section. That is, in the rolled configuration, the condom includes a ring-like roll having multiple layers of the medial section of the body being wound about the first end rib. As the rib is initially rolled over the outer side of the body medial section, the outer side of the body medial section is disposed immediately adjacent to the rib. Thus, the exposed side of the roll is the inner side of the body medial section. With each revolution of the roll, the inner side of the body medial section is placed into contact with the exposed section of the roll while the corresponding inner side of the body medial section, i.e. the outer side of the body medial section directly opposite the inner side of the body medial section that is being placed into contact with the exposed section, becomes the outer side of the roll.

In this configuration, the second, closed end of the condom is not part of the roll and extends across the opening in the roll. The roll may be said to have an upper side and a lower side. The roll upper side includes the outer side of the second, closed end while the lower side includes the inner side of the second, closed end. As noted above, the roll always has a section of the inner side of the body medial section exposed. Thus, to wear the condom correctly, the user must unroll the condom with the lower side, and therefore the inner side of the second closed end and medial section, contacting the penis.

Users often have difficulty orienting the condom properly with the lower side of the roll facing downwardly. That is, the upper and lower sides of a rolled condom have a nearly identical appearance. Thus, users who are often distracted by the associated physical activity and/or may be in a dim or dark area, may attempt to put on the condom with the upper side, and therefore the outer surface of the condom, against the penis. Due to the direction of the roll, the condom cannot be unrolled when it is put on upside down.

While the mis-orientation of the condom is easily corrected, many users find such fumbling with a prophylactic device to interrupt what is, hopefully, a passionate activity. As such, many users choose to forego use of a condom and thereby potentially expose themselves, and their partners, to various diseases and the possibility of pregnancy.

SUMMARY OF THE INVENTION

The present invention discloses a condom having an indicia disposed on the lower side of the roll when the condom is in the rolled configuration. Preferably, the indicia is a fluorescent marking disposed on the inner side of the condom disposed at a location so that, when the condom is in the rolled configuration, the indicia is visible from the lower side only. More preferably, the indicia is a ring-shaped marking extending about the inner side of the tubular body. In this configuration, a user holding the condom can easily determine which is the upper side of the roll and which is the lower side of the roll. The user may then quickly orient the condom with the lower side facing toward the penis and unroll the condom in the proper direction.

BRIEF DESCRIPTION OF THE DRAWINGS

A full understanding of the invention can be gained from the following description of the preferred embodiments when read in conjunction with the accompanying drawings in which:

FIG. 12 is an alternate bottom view of a specific indicia;
FIG. 12A is a partial side view of the condom shown in FIG. 12.
FIG. 13 is an alternate bottom view of a specific indicia.

DESCRIPTION OF THE PREFERRED EMBODIMENTS

As used herein, the "user" is the male wearing the condom and, as described, is the person handling the condom. It is understood that a condom may be handled by someone other than the person wearing the condom.

As used herein, "fluorescent" shall mean any very bright and/or dazzling color and does not require the color and/or substrate to fluoresce.

Figure 1:
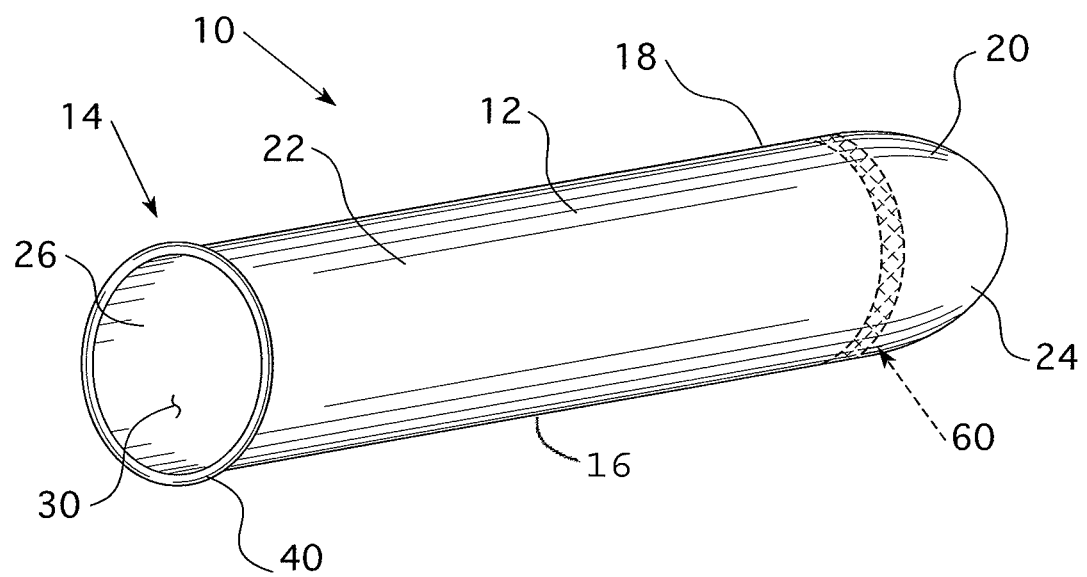
FIG. 1 is an isometric view of a condom.
Figure 4:
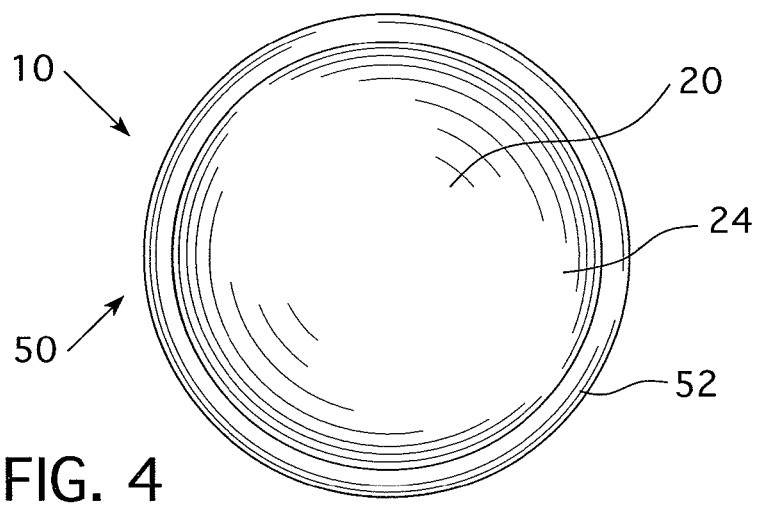
FIG. 4 is a top view of a rolled condom.
Figure 5:
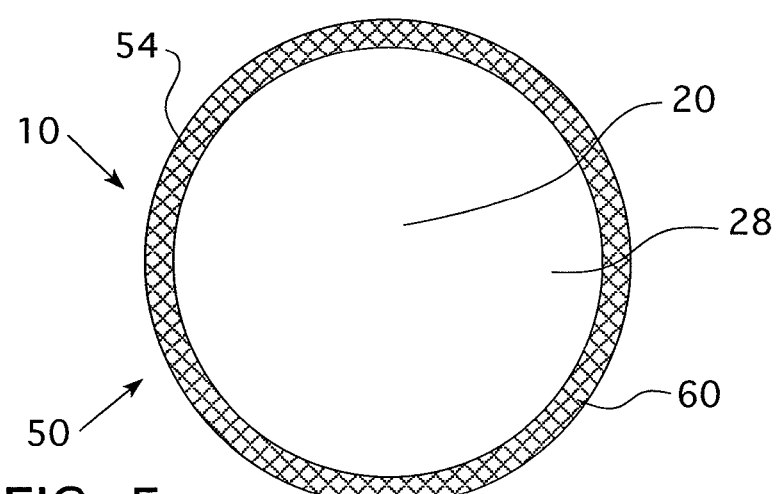
FIG. 5 is a bottom view of a rolled condom.

As shown in FIG. 1, a condom 10 is shown in a second, unrolled configuration. As described below, and as shown in FIGS. 4 and 5, the condom 10 is typically stored in a first, rolled configuration. The condom 10, which is typically made from a thin, elastic latex or plastic, has a generally circular tubular body 12 having an open first end 14, an elongated medial section 16, a second end 18 and a closed second end section 20. The closed second end section 20 is coupled to, and preferably formed as an integral part of, the body second end 18. The closed second end section 20, preferably, is shaped as a convex dome. The body 12 and the closed second end section 20 each have an outer side 22, 24 and an inner side 26, 28 (FIG. 5), respectively. Preferably, the body outer side 22 and the second end section outer side 24 form a contiguous surface. Similarly, the body inner side 26 and the second end section inner side 28 preferably form a contiguous surface. Thus, the body 12 and the closed second end section 20 define a generally enclosed space 30. The body first end 14 preferably includes a reinforced rib 40. The rib 40 is shaped as a generally circular torus and is made from the same material as the body 12. Typically, the rib 40 is formed as an integral part of the body first end 14.

Figure 2:
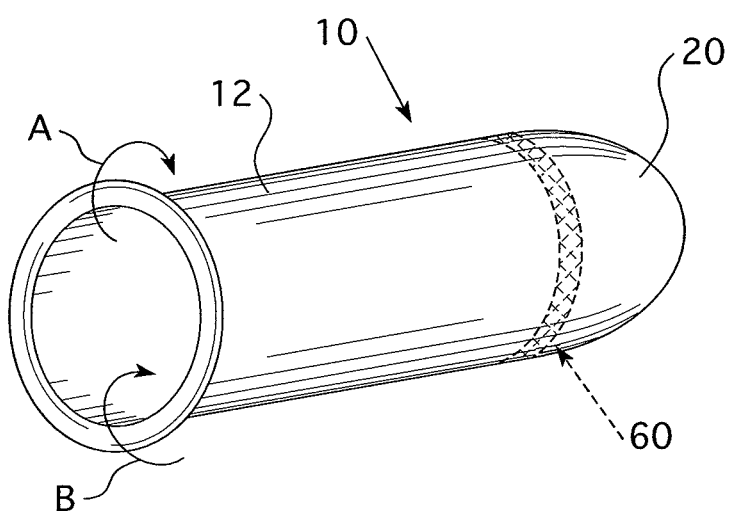
FIG. 2 is an isometric view of a partially rolled condom.
Figure 3:
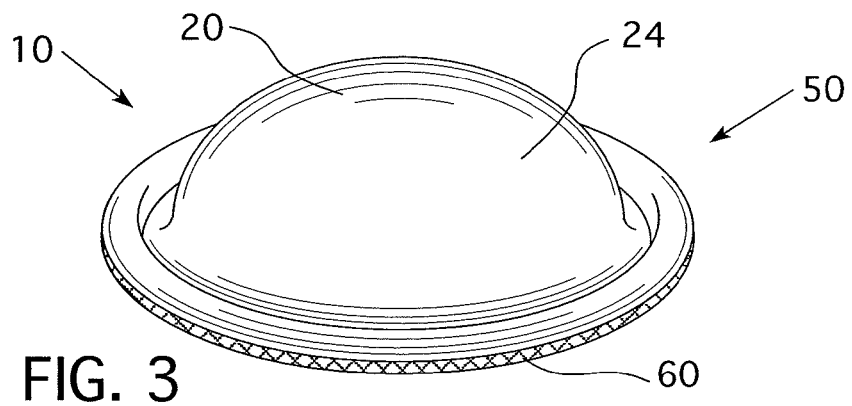
FIG. 3 is an isometric view of a rolled condom.

The condom 10, as noted above, is typically stored in a first, rolled configuration. Thus, after the condom 10 is formed, typically on an elongated mandrill, the condom 10 is rolled as shown in FIG. 2 as indicated by the arrow "A." That is, the body first end 14 and/or the rib 40 is rolled over the body outer side 22. The body first end 14, and/or the rib 40, is rolled over substantially all of the body medial section 16. The process of rolling the condom 10 creates a roll 50, as shown in FIGS. 3-5, that is a generally circular torus having multiple layers of the body medial section 16 wound about the body first end 14 and/or the rib 40. Further, when substantially all of the body medial section 16 has been rolled about the body first end 14 and/or the rib 40, the roll 50 is generally planar having an upper side 52 and a lower side 54, as shown in FIGS. 4 and 5, respectively. When a condom 10 is put on, the user typically orients the roll 50 so that the lower side 54 is disposed at the tip of an erect penis and unrolls the condom 10 downwardly as indicated by arrow "B" in FIG. 2.

The condom 10 further includes an indicia 60, best shown in FIG. 5, disposed on the roll lower side 54. The indicia 60 provides a visual indication as to the orientation of the roll 50. That is, the indicia 60 is generally not visible when the roll 50 is viewed from a position generally normal to the roll upper side 52. Thus, a user simply orients the roll 50 so that the user cannot see the indicia 60 and then unrolls the condom 10 as described above. Preferably, the indicia 60 is fluorescent so that it may be easily seen, even in low light conditions. The indicia 60 may be printed, or otherwise applied, to the body inner side 26, or on the second end section inner side 28, adjacent to the body second end 18. Alternatively, the indicia 60 may be incorporated into the body 12. For example, a dye may be injected into the liquid latex used to form the condom 10. The indicia 60 is positioned so that, when the condom 10 is in the rolled configuration, the indicia 60 is disposed on the roll lower side 54. It is noted that, as shown in FIG. 1, the indicia 60 may be partially visible through the body 12. It is further noted that, when the condom 10 is in the rolled configuration, the indicia 60 is not clearly visible, or may not be visible at all, through the multiple layers that comprise the roll 50. Further, while the indicia 60 may have any shape or characteristics, in the preferred embodiment, the indicia 60 is a solid mark extending generally about the circumference of the lower side 54 of the roll 50.

Figure 6:
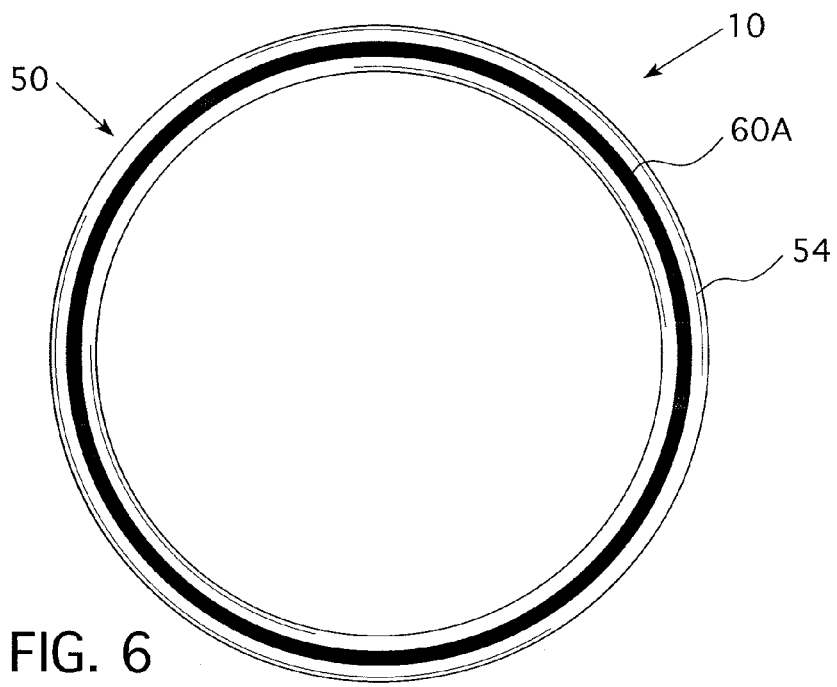
FIG. 6 is an alternate bottom view of a specific indicia.
Figure 7:
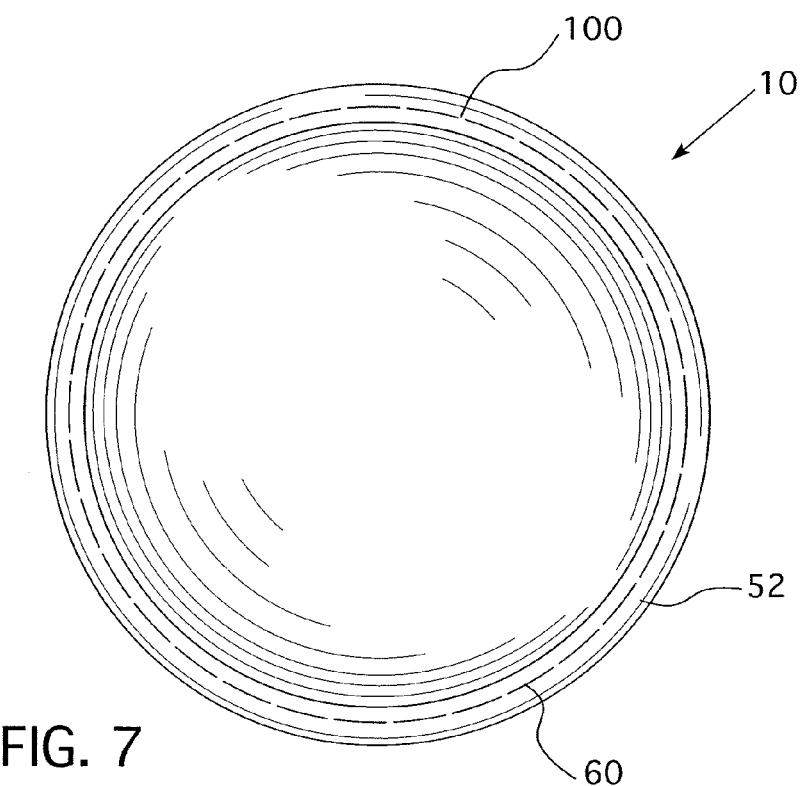
FIG. 7 is an alternate top view of a specific indicia.
Figure 8:
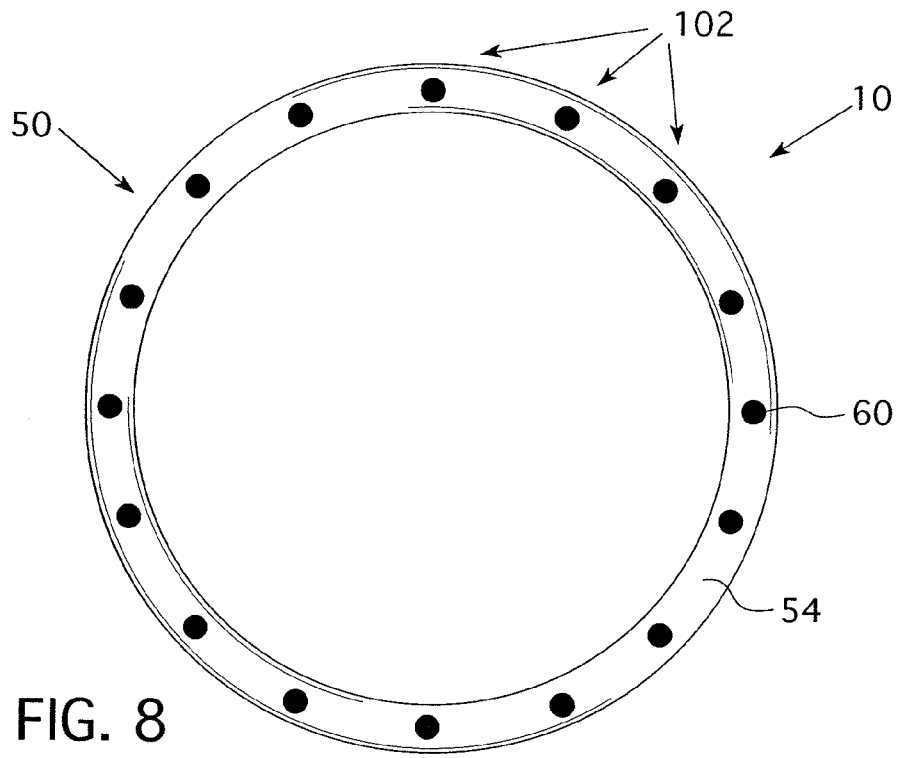
FIG. 8 is an alternate bottom view of a specific indicia.
Figure 9:
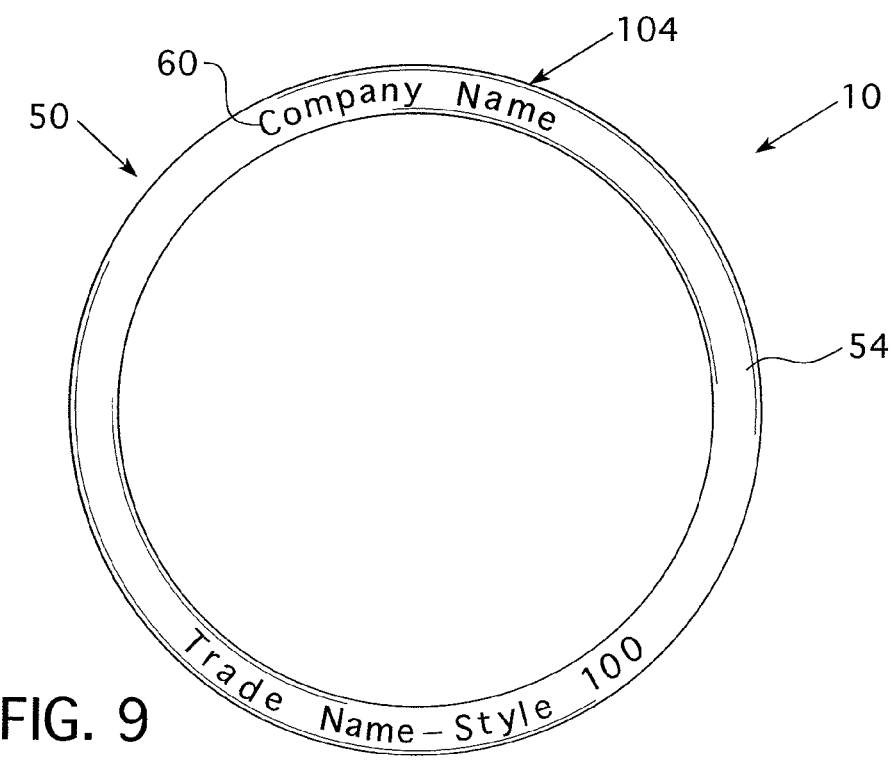
FIG. 9 is an alternate bottom view of a specific indicia.
Figure 10:
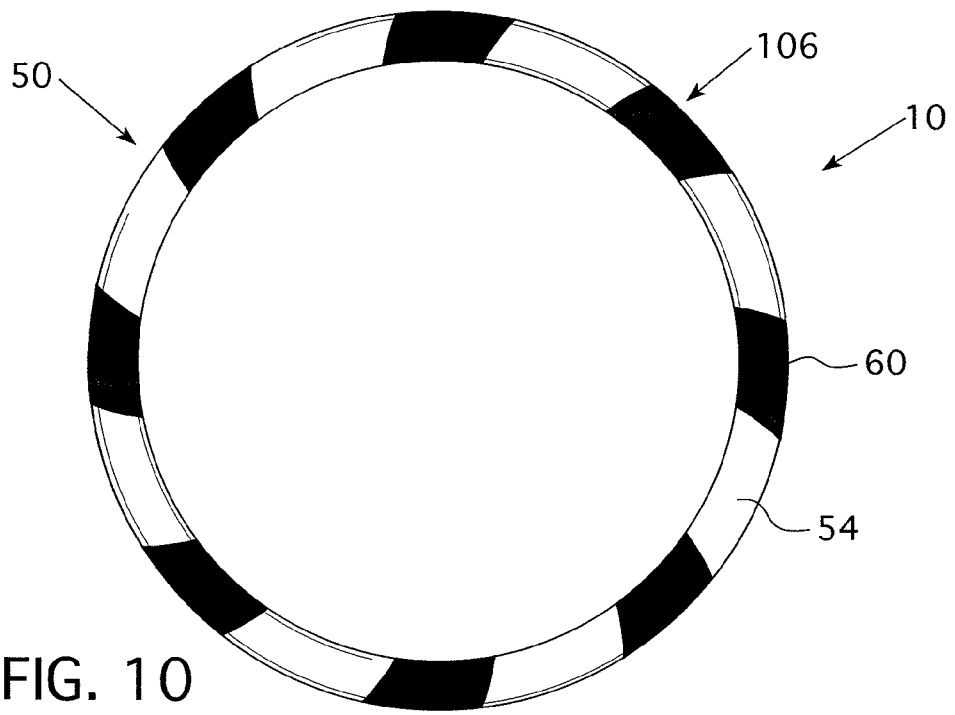
FIG. 10 is an alternate bottom view of a specific indicia.
Figure 11:
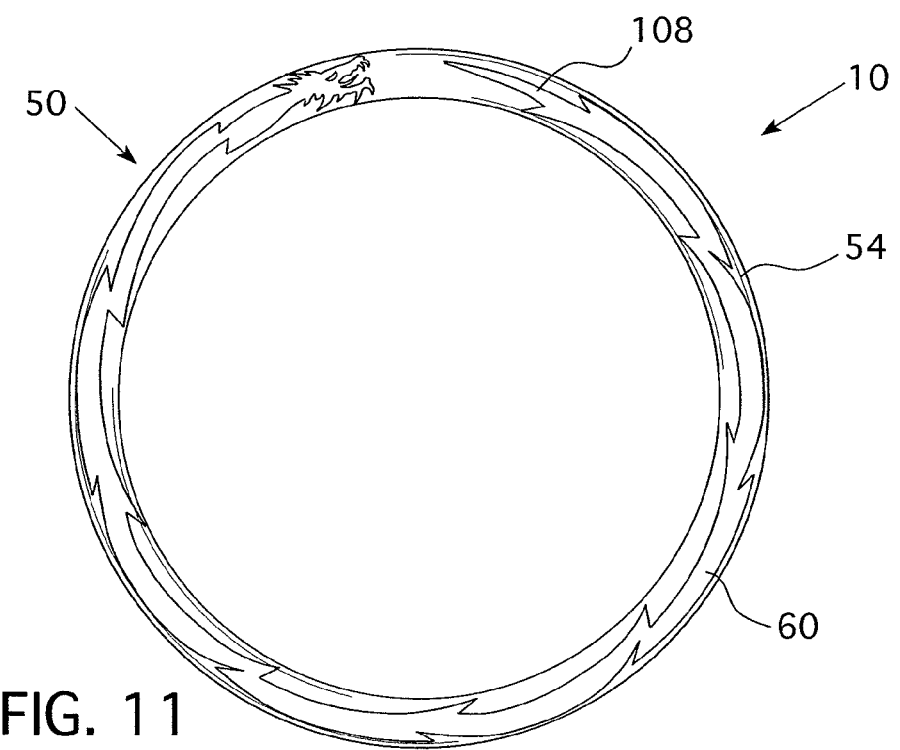
FIG. 11 is an alternate bottom view of a specific indicia.

It is noted that while the preferred indicia 60 is at least one solid ring 60A (FIG. 6), the indicia 60 may have any shape and/or characteristics so long as the indicia 60 provides a visual indication as to the orientation of the roll 50. Thus, as shown in FIGS. 7-11, the indicia 60 may be selected from the group including an intermittent pattern, such as, but not limited to, a series of dashed lines 100 (FIG. 7), a dotted pattern 102 (FIG. 8), alphanumeric text 104 (FIG. 9), a repeating pattern 106 (FIG. 10, as shown, a "candy cane" pattern), a design 108 (FIG. 11, as shown, a dragon), or any combination thereof.

Figure 14:
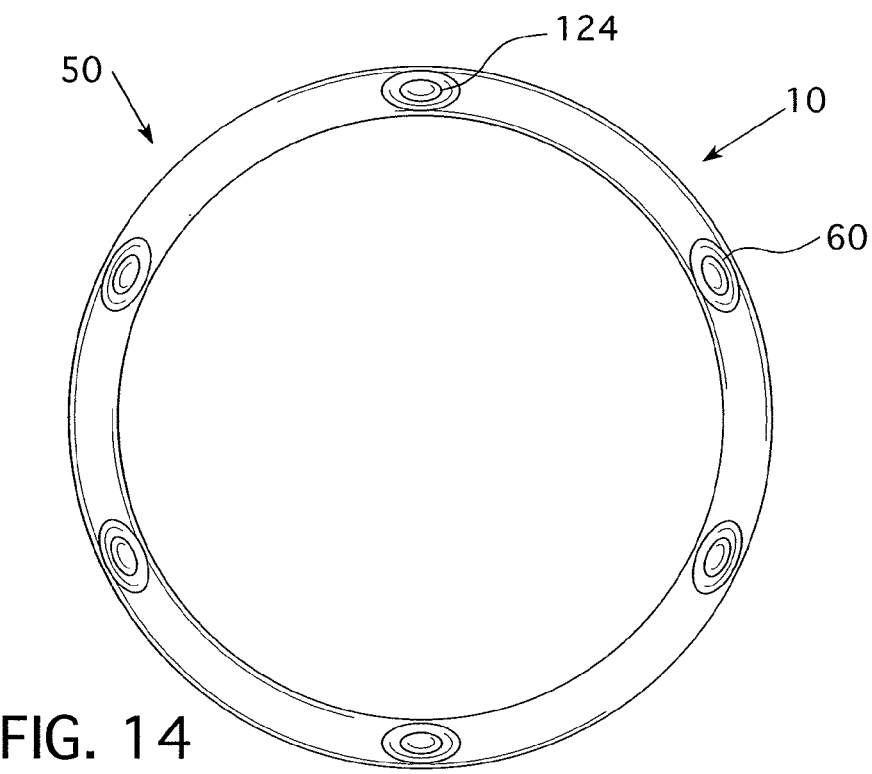
FIG. 14 is an alternate bottom view of a specific indicia.

Further, the indicia 60 may be created by an alteration in the thickness of the body 12. That is, a body 12 made of latex, or similar material, tends to be generally smooth. Thus, a visual indicia 60 may also be created by providing deformation 110 to the body 12. The deformation 110 may be of any type, but, as a condom body 12 is typically thin, preferably the deformation 110 is an intermittent thickening or raised portions on the body 12, i.e. one or more "bumps" on the body 12. More preferably the deformation 110 forms a repeating pattern so that it may be more easily seen. Thus, as shown in FIGS. 12-14, the indicia 60, that is, the deformation 110, may be a pattern of intermittent raised portions 123 selected from the group including: a dashed circular line 120 (FIG. 12), a plurality of dots 122 (FIG. 13), or a plurality of ovals 124 (FIG. 14). Such an indicia 60 has a visual as well as a tactile element. That is, in addition to being visible, the indicia 60 may be felt, for example, by running a finger over the indicia 60. Thus, the user may determine the orientation of the roll 50 via a tactile feedback. It is noted that other forms of tactile feedback may be provided, e.g. electrical stimulation and ultrasound feedback.

Figure 15:
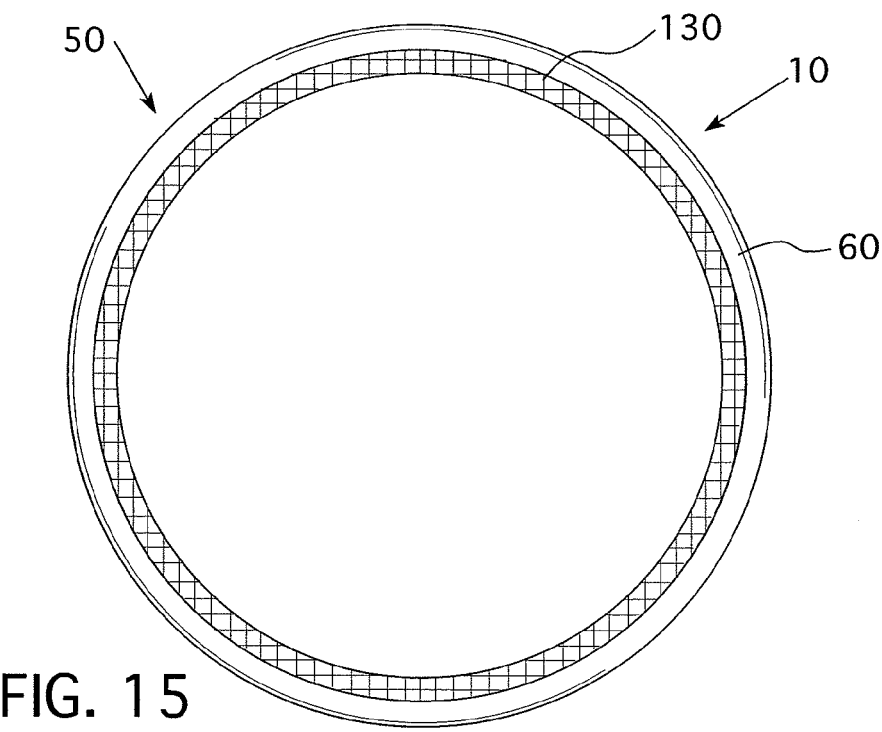
FIG. 15 is an alternate bottom view of a specific indicia.
Figure 16:
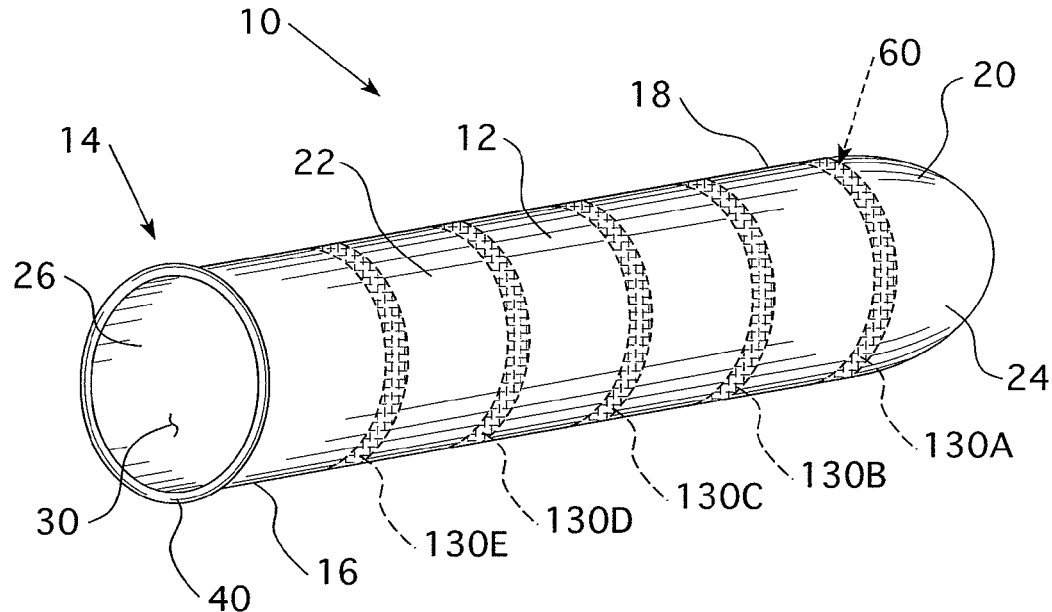
FIG. 16 is an alternate isometric view of a specific indicia.

The indicia 60 may be formed by, or incorporated with, a material 130 structured to perform an additional function. The material 130 may be, but is not limited to, an adhesive, a lubricant, an anesthetizing agent, and an enhancement agent. An enhancement agent may be a drug or other pharmacological compound. Materials such as these, e.g. an adhesive or a drug structured to enhance an erection, should decrease the chance of having the condom 10 slip off the penis or rupture, therefore increasing the effectiveness and safety of the condom 10. The material 130 may naturally have a noticeable color or be florescent, or, the material 130 may have a dye or similar coloring agent added thereto. As shown in FIG. 15, the material 130, preferably, extends substantially over the circumference on one side of the roll 50. That is, while a continuous ring of material 130 is preferred, the material 130 may be applied in a pattern such as, but not limited to, a broken ring (not shown). Further, there may be more than one area of material 130 disposed on the body inner side 26. In this embodiment, shown in FIG. 16, the material 130 is, preferably, applied in a series of spaced rings 130A, 130B, 130C, etc., located on the body inner side 26 and extending substantially over the circumference of the body inner side 26. The material ring 130A closest to the closed second end section 20 in the unrolled configuration becomes the indicia 60 in the rolled configuration, hereinafter the "primary ring 130A." Thus, if the material 130 is visible through multiple layers of the roll 50, the location of the additional material rings 130B, 130C, 130D, 130E is structured so that the material 130 is aligned on the same side of the roll 50 as the primary ring 130A when the body is rolled. Alternatively, if the material 130 cannot be seen through the layers of the roll 50, the material 130 may be disposed anywhere in the body inner side 26 so long as the primary ring 130A is the only visible indicia 60.

It is noted that, if the material 130 is an adhesive 132, the adhesive 132 is, preferably, weak, i.e. the adhesive 132 may be easily peeled away from skin while still helping to maintain the condom 10 in place during use. The adhesive 132 may serve an additional purpose. That is, like the "bumps" discussed above, the adhesive 132 provides a tactile indication of the orientation of the condom roll 50. Thus, the user may determine the orientation of the roll 50 via a tactile feedback.

Figure 17:
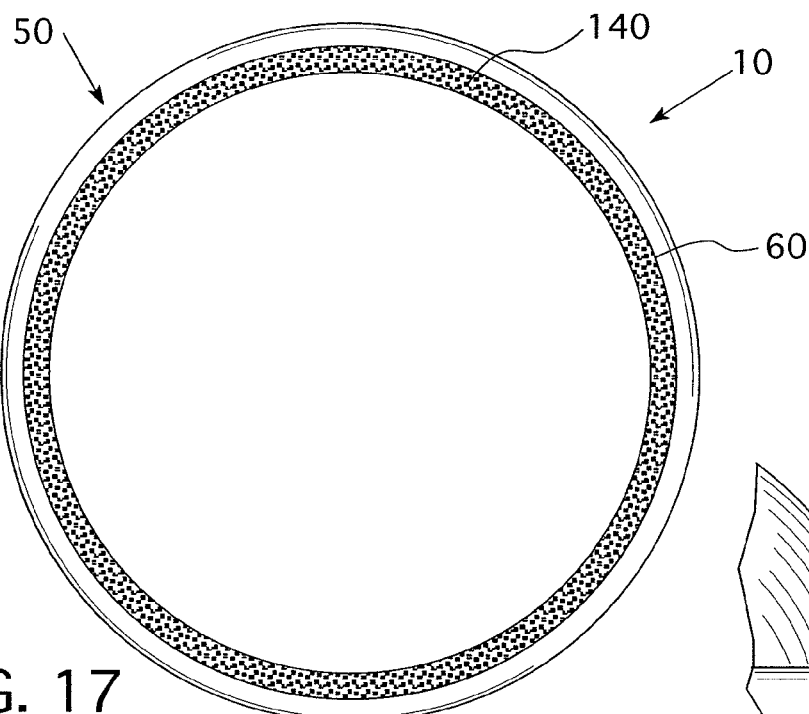
FIG. 17 is an alternate bottom view of a specific indicia.
Figure 17A:
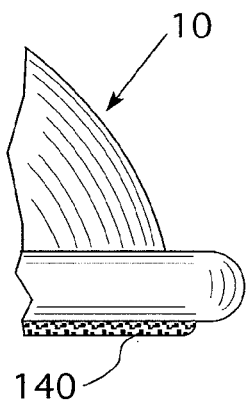
FIG. 17A is a partial side view of the condom shown in FIG. 17.

As shown in FIG. 17, the indicia 60 may also be created from a reactive-luminescent material(s) 140. That is, the indicia 60 may be made from a material 140 that glows when exposed to light, typically identified as a "glow-in-the-dark" material, or a second material 142, as in carnival "glowsticks." If the reactive-luminescent material 140 is non-liquid and stable, it may be applied to the body inner side 26 in a manner similar to ink.

Figure 18:
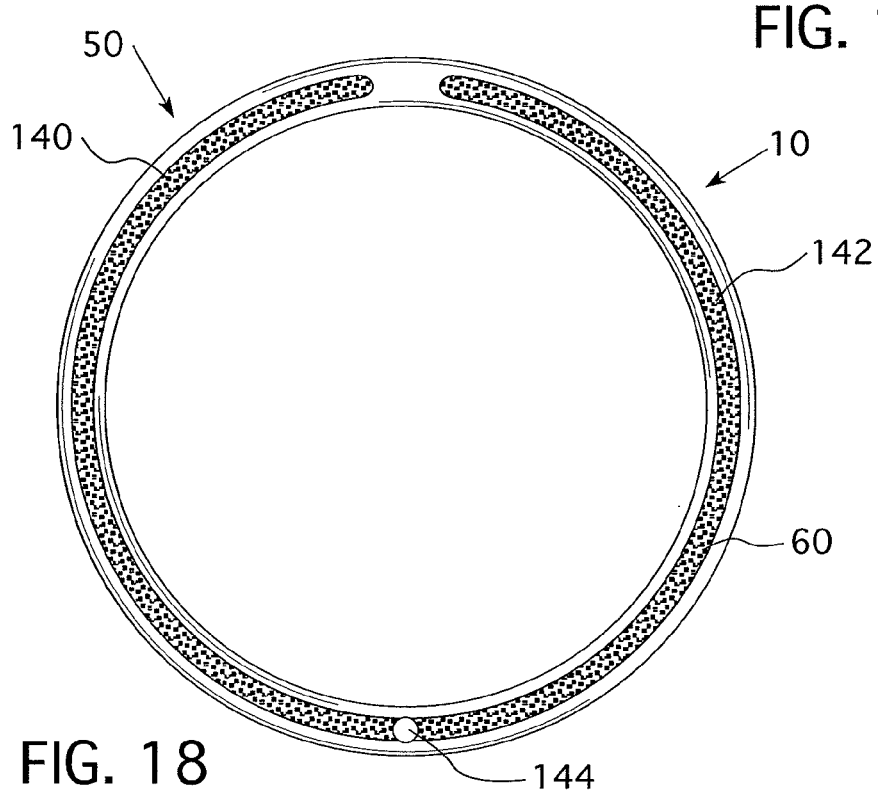
FIG. 18 is an alternate bottom view of a specific indicia.

As shown in FIG. 18, if the indicia 60 is formed from two reactive-luminescent materials, a first reactive-luminescent material 140 and a second reactive-luminescent material 142, the reactive-luminescent materials 140, 142 are typically liquids that must be combined, as in "glow sticks." So as to accommodate the two reactive-luminescent materials 140, 142, the body 12 may include a circumferential plenum 143. The plenum 143 is positioned on the body 12 so that, when the condom 10 is configured as a roll 50, the plenum 143 is visible from only one side of the roll 50. The circumferential plenum 143, preferably, does not extend all the way around the body inner side 26 while still extending substantially about the body inner side 26, i.e. the plenum 143 is not a continuous ring. The plenum 143 may include a deformable barrier 144, e.g. a wax bead, therewithin structured to separate two liquids. The reactive-luminescent materials 140, 142 are disposed within the plenum 143 on opposite sides of the deformable barrier 144. When the barrier 144 is deformed or torn, the two liquids may combine and luminesce.

As discussed above, the indicia 60 is preferably fluorescent. However, other color schemes may also act so as to provide a visual indication as to the orientation of the roll 50. It is known that certain multi-color combinations, identified as high-contrast color schemes, are more likely to be seen/noticed by a human than other color schemes. High contrast color schemes are found both in nature, e.g. on venomous snakes and insects, as well as human made objects, e.g. road signs. High-contrast color schemes include, but are not limited to, black-yellow, black-white, and white-green. The color of the body 12 and the indicia 60 may be any high-contrast color scheme wherein the body 12 is a first color and the indicia 60 is a second color and wherein the first and second colors are a high-contrast color scheme. For example, the body 12 may be black and the indicia 60 may be yellow, or, conversely, the body 12 may be yellow and the indicia 60 may be black. Alternatively, as shown in FIG. 19, at least two high contrast colors 146, 148 disposed in alternating bands may form the indicia 60.

Figure 19:
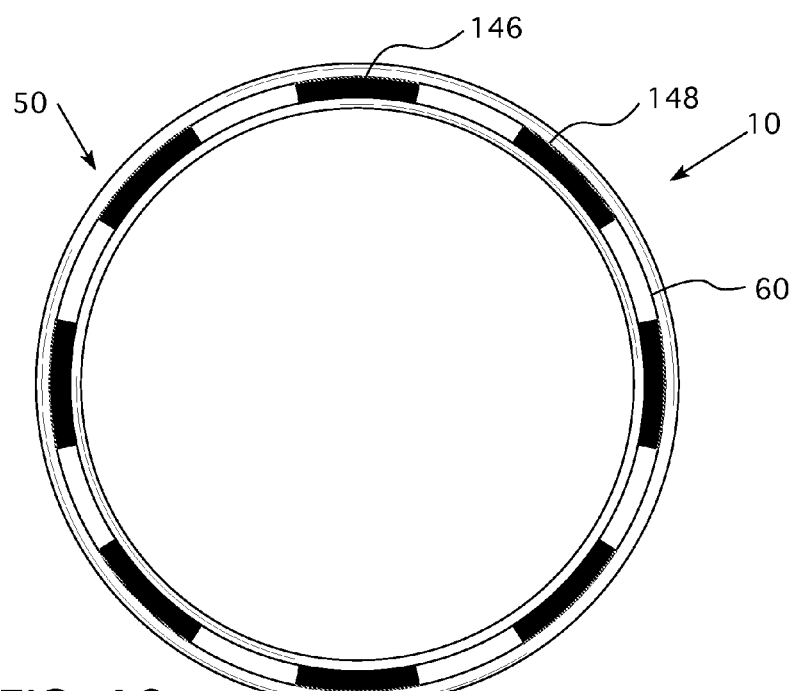
FIG. 19 is an alternate bottom view of a specific indicia.
Figure 20:
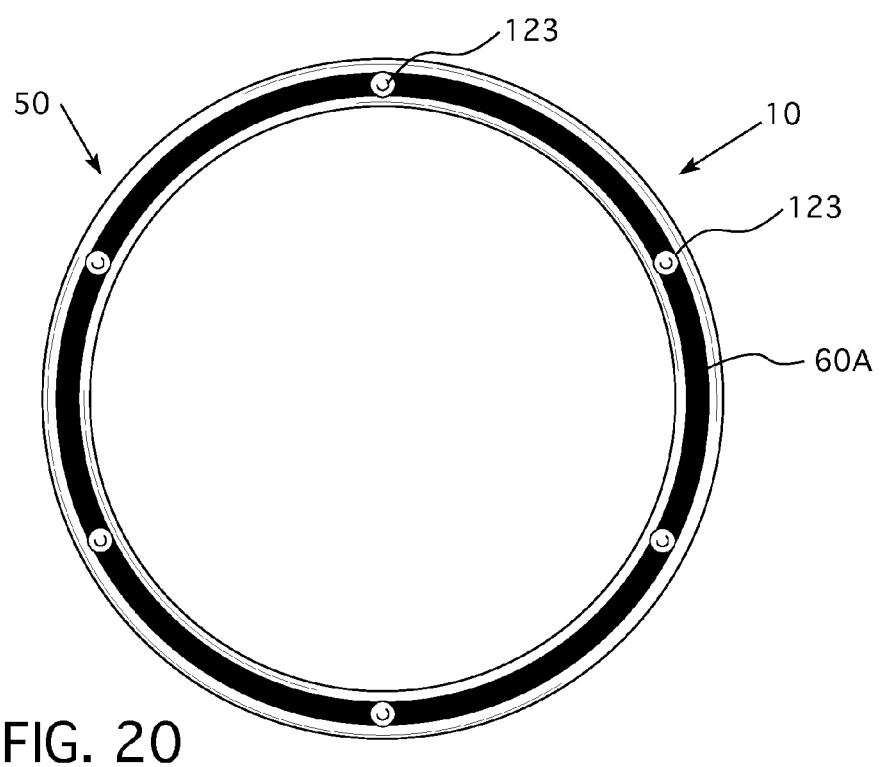
FIG. 20 is an alternate bottom view of a specific indicia.

As shown in FIG. 19, the indicia 60 may also be an optically variable device 150, such as, but not limited to a hologram or similar security devices. An optically variable device 150 may be dazzling or not depending upon the viewing angle and the angle of the light applied to the indicia 60. The optically variable device 150 may be incorporated into a foil 152, or other thin, flexible material which is then coupled to the body 12. Alternately, the optically variable device 150 may be imprinted upon the body 12 itself. The optically variable device 150 may take any of the forms of the indicia 60 discussed above. That is, the optically variable device 150 may be a complete ring, a plurality of dots or dashes, a pattern, or may include a design. Similarly, it is noted that any of the different forms of the indicia 60 described above may be combined. For example, the indicia 60 could include, but is not limited to, a solid ring 60A disposed over a pattern of intermittent raised portions 123 (FIG. 20).

While specific embodiments of the invention have been described in detail, it will be appreciated by those skilled in the art that various modifications and alternatives to those details could be developed in light of the overall teachings of the disclosure. For example, as noted above the indicia 60 is disclosed as providing an indication of orientation. In the preferred embodiment the indicia is disposed on the roll lower side 54. An equivalent design may have the indicia 60 on the roll upper side 52. That is, as long as the indicia 60 is on only one side of the roll, the indicia 60 provides an indication of orientation. Accordingly, the particular arrangements disclosed are meant to be illustrative only and not limiting as to the scope of invention which is to be given the full breadth of the claims appended and any and all equivalents thereof.

What is claimed is:

1. A condom comprising:
    a tubular body having a closed end and configured as a roll;
    an indicia on said roll, said indicia providing a visual indication as to the orientation of said roll;
    said roll is a generally circular torus, said roll having an upper side and a lower side;
    said indicia extends about one of said upper side or said lower side;
    wherein said indicia indicates the orientation of said roll via a tactile feedback; and
        wherein said indicia is created by an alteration in the thickness of the body.

2. The condom of claim 1 wherein said indicia is a thickening of the body forming intermittent raised portions.

3. The condom of claim 2 wherein said intermittent raised portions form a pattern selected from the group including: a dashed circular line, a plurality of dots, or a plurality of ovals.

4. A condom comprising:
    a thin, elastic, generally tubular body having an open first end and an elongated medial section, said body having an inner side and an outer side;
    a closed second end section having an inner side and an outer side, said closed second end section coupled to said body, whereby said body and said closed second end section defining a generally enclosed space;
    said body structured to be reconfigured from a first rolled configuration, wherein said first end is rolled over said outer side of substantially all of said elongated medial section, to a second unrolled configuration, wherein said elongated medial section is substantially unrolled from said first end;
    wherein, when said body is in said first rolled configuration, said elongated medial section is rolled, generally snugly, about said first end thereby creating a roll, said roll having an upper side and a lower side;
    an indicia disposed on said roll, said indicia providing a visual indication as to the orientation of said roll;
    said indicia extends about one of said roll upper side or said roll lower side; and
    wherein said indicia is formed by a material structured to perform an additional function, said material selected from the group including: an adhesive, a lubricant, an anesthetizing agent, and an enhancement agent.

5. The condom of claim 4 wherein said material is disposed on the body inner side in a series of spaced rings.

6. A condom comprising:
    a tubular body having a closed end and configured as a roll;
    an indicia on said roll, said indicia providing a visual indication as to the orientation of said roll;
    said roll is a generally circular torus, said roll having an upper side and a lower side;
    said indicia extends about one of said upper side or said lower side;
    wherein said indicia is formed by a material structured to perform an additional function; and wherein said material is selected from the group including: an adhesive, a lubricant, an anesthetizing agent, and an enhancement agent.

7. A condom comprising:
a tubular body having a closed end and configured as a roll;
an indicia on said roll, said indicia providing a visual indication as to the orientation of said roll;
said roll is a generally circular torus, said roll having an upper side and a lower side;
said indicia extends about one of said upper side or said lower side;
wherein said indicia is formed by a material structured to perform an additional function; and;
wherein said material is disposed on the body inner side in a series of spaced rings.

8. A condom comprising:
a tubular body having a closed end and configured as a roll;
an indicia on said roll, said indicia providing a visual indication as to the orientation of said roll;
said condom includes a circumferential plenum disposed on the body inner side adjacent to the body second end;
said circumferential plenum extending substantially about the body inner side while not being a continuous ring;
a deformable barrier disposed within said plenum, said barrier structured to separate two liquids;
a first reactive-luminescent material disposed within said plenum on one side of said bather; and
a second reactive-luminescent material disposed within said plenum on the other side of said barrier.

* * * * *

UNITED STATES PATENT AND TRADEMARK OFFICE
CERTIFICATE OF CORRECTION

| | | |
|---|---|---|
| PATENT NO. | : 8,646,451 B2 | Page 1 of 1 |
| APPLICATION NO. | : 12/642897 | |
| DATED | : February 11, 2014 | |
| INVENTOR(S) | : William Thomas Mistler | |

It is certified that error appears in the above-identified patent and that said Letters Patent is hereby corrected as shown below:

In the Claims

Column 7, line 27, Claim 8, "bather" should read --barrier--.

Signed and Sealed this
Twenty-fifth Day of August, 2015

Michelle K. Lee
*Director of the United States Patent and Trademark Office*